United States Patent
Shifrine

(10) Patent No.: US 10,413,556 B1
(45) Date of Patent: Sep. 17, 2019

(54) PRODUCTION OF INSULIN BY TESTOSTERONE OLFACTION

(71) Applicant: Moshe Shifrine, Santa Fe, NM (US)

(72) Inventor: Moshe Shifrine, Santa Fe, NM (US)

( * ) Notice: Subject to any disclaimer, the term of this patent is extended or adjusted under 35 U.S.C. 154(b) by 0 days.

(21) Appl. No.: 16/360,824

(22) Filed: Mar. 21, 2019

(51) Int. Cl.
*A61K 31/568* (2006.01)
*A61K 31/5685* (2006.01)
*A61K 38/28* (2006.01)
*A61K 9/00* (2006.01)

(52) U.S. Cl.
CPC .......... *A61K 31/5685* (2013.01); *A61K 9/007* (2013.01); *A61K 38/28* (2013.01)

(58) Field of Classification Search
None
See application file for complete search history.

(56) References Cited

U.S. PATENT DOCUMENTS

| | | | | |
|---|---|---|---|---|
| 8,679,507 B2 * | 3/2014 | Shifrine | ............... | A61K 39/36 424/195.15 |
| 2002/0061869 A1 * | 5/2002 | Lichten | ............... | A61K 31/00 514/178 |
| 2004/0077540 A1 * | 4/2004 | Quay | ............... | A61K 9/0043 424/94.64 |

OTHER PUBLICATIONS

Zaghloul H. et al. Association Between Diabetes Mellitus and Olfactory Dysfunction. Diabetic Medicine 35(1)41-52, 2018. (Year: 2018).*

Coleman D. et al. Effect of Genetic Background on the Therapeutic Effects of DHEA in Diabetes Obesity Mutants and in Aged Normal Mice. Diabetes 33(1)26-32, 1984. (Year: 1984).*

Mauriello J. et al. Testosterone—A Pharmaceutical Adjunct in the Treatment of Leg Ulcers. J of Advancement in Medicine 10(2)129-137, Summer 1997. (Year: 1997).*

Lee, C. et al. The Effect of Testosterone Supplement on Insulin Sensitivity, Glucose Effectiveness, and Acute Insulin Response After Glucose Load in Male Type 2 Diabetes. Endocrine Research 31(2)139-148, 2005. (Year: 2005).*

Pitteloud N. et al. Relationship Between Testosterone Levels, Insulin Sensitivity, and Mitochondrial Function in Men. Diabetes Care 28(7)1636-42, Jul. 2005. (Year: 2005).*

Davison S. et al. Pharmacokinetics and Acute Safety of Inhaled Testosterone in Postmenopausal Women. Pharmacokinetics and Pharmacodynamics 45:177-184, 2005. (Year: 2005).*

Banks, W. et al. Delivery of Testosterone to the Brain by Intranasal Administration. J of Drug Targeting 17(2)91-97, Feb. 2009. (Year: 2009).*

Dhindsa S. et al. Insulin Resistance and Inflammation in Hypogonadotropic Hypogonadism and Their Reduction After Testosterone Replacement in Men with Type 2 Diabetes. Diabetes Care 39:82-91, Jan. 2016. (Year: 2016).*

Grossmann M. Testosterone and Glucose Metabolism in Men. Endocrinology 220(3)R37-R55, 2014. (Year: 2014).*

* cited by examiner

*Primary Examiner* — Ralph J Gitomer
(74) *Attorney, Agent, or Firm* — Kohn and Associates PLLC

(57) ABSTRACT

A method of inducing the production of insulin in the body by an individual smelling a composition of a solution including testosterone, and inducing the production of insulin in the body of the individual. A method of treating diabetes type 2 by an individual having diabetes type 2 smelling a composition of a solution including testosterone, inducing the production of insulin in the body of the individual, and treating diabetes type 2 in the individual.

7 Claims, No Drawings

PRODUCTION OF INSULIN BY TESTOSTERONE OLFACTION

BACKGROUND OF THE INVENTION

1. Technical Field

The present invention relates to methods and compositions for reducing blood sugar. More specifically, the present invention relates to reducing blood sugar through testosterone olfaction.

2. Background Art

Olfaction, the sense of smell, is critical for the survival of almost all creatures. Humans are able to distinguish over 10,000 different odor molecules. With every inhalation, currents of air swirl through the nostrils over the bony turbinates in the nose that contain receptors in the olfactory epithelium. Olfactory mucosa protects the olfactory epithelium and allows odors to dissolve for detection by olfactory receptors. The cilia projecting from the olfactory knob contain receptors for odorants. The cilia project from the knob directly into the atmosphere. The interaction of the right molecule with the right receptor causes a structural transformation of the receptor, which gives rise to an electrical signal to the olfactory bulb and thence to the areas in the limbic brain that perceive it as the original smell. It has previously been demonstrated by Applicant that olfaction (i.e. smelling) truffle extract containing testosterone initiates production of free testosterone in clinically significant amounts in U.S. Pat. No. 8,679,507.

Later, Applicant determined that olfaction of pure testosterone (Prescription, Walgreen Pharmacy) does initiate testosterone production (unpublished research). These studies raised the question: is this action by olfaction unique to testosterone or can the effect be observed with other hormones? To answer this question, Applicant studied progesterone olfaction in 10 postmenopausal women. Progesterone is the primary female sex hormone and testosterone is the primary male sex hormone. Progesterone olfaction test results demonstrated conclusively that olfaction does initiate production of progesterone in post-menopausal women (unpublished studies). This is a ground-breaking discovery: smelling the hormones that have been tested caused the body to produce the hormone that is smelled. However, it is still unknown whether hormone olfaction will work with hormones other than sex hormones.

Diabetes is a serious chronic disease that occurs when the pancreas does not produce enough insulin (diabetes type 1) or when the body cannot effectively use the insulin produced (diabetes type 2). According to the American Diabetes Association, in 2017 an estimated 33 million American people had diabetes. That is 10 percent of the U.S. population. It is more prevalent in the black and Hispanic populations than among whites. The total estimated cost of diagnosed diabetes in 2017 was $327 billion. People diagnosed with diabetes on average have an annual medical expenditure of $9,600. Globally, an estimated 422 million adults were living with diabetes in 2014, compared to 108 million in 1980.

In diabetes type 1, there is an autoimmune-mediated destruction of insulin-producing β-cells in the pancreas, resulting in absolute insulin deficiency. Without receiving insulin, diabetes type 1 patients will fall into coma and die. The type of insulin they need can only be administered with a syringe, insulin pump, or insulin pen.

In diabetes type 2, there is either inadequate insulin production by the β-cells or insulin resistance or both because of reasons not completely understood. Patients with type 2 diabetes have relatively low insulin production or develop insulin resistance. The insulin receptors resist the instructions from insulin, and they don't properly process blood glucose. This leads to elevated blood sugar which then requires insulin shots. Diabetes type 2 is one of the leading causes of death in the world. Both cases, diabetes type 1 and diabetes type 2, require adding insulin to the patient's body.

Grossman (Testosterone and glucose metabolism in men: current concepts and controversies. (J. Endocrinol. 2014 Jan. 27, 220(3)R37-55)) describes studies that show that low testosterone is associated with insulin resistance and with increased risk of diabetes. Definitive evidence is currently lacking that low testosterone associated with disorders of glucose metabolism is causative.

Dhindsa, et al. (Insulin Resistance and Inflammation in Hypogonadotropic Hypogonadism and Their Reduction After Testosterone Replacement in Men With Type 2 Diabetes. Diabetes Care. 2016 January; 39(1): 82-91) describes the long term effects of giving testosterone by injection. The study is a randomized placebo-controlled trial to evaluate the effect of testosterone on insulin resistance in men with diabetes type 2. Participants in the trial included 94 type 2 diabetic men among whom 44 had low testosterone levels. Participants with low testosterone received weekly testosterone injections for 24 weeks. When the men were given testosterone their ability to utilize insulin was improved.

H. Zughlout, et al. (Association between diabetes mellitus and olfactory dysfunction: current perspective and future directions. Diabet. Med 35, 41-52(2018)) provides a review of olfaction and its dysfunction in diabetes. There is no disclosure or suggestion of using testosterone olfaction with diabetes patients.

There remains a need for treatments for diabetes, especially ones that are easy to use.

SUMMARY OF THE INVENTION

The present invention provides for a method of inducing the production of insulin in the body by an individual smelling a composition of a solution including testosterone, and inducing the production of insulin in the body of the individual.

The present invention also provides for a method of treating diabetes type 2 by an individual having diabetes type 2 smelling a composition of a solution including testosterone, inducing the production of insulin in the body of the individual, and treating diabetes type 2 in the individual.

DETAILED DESCRIPTION OF THE INVENTION

The present invention provides for compositions and methods for inducing the production of insulin in the body of an individual through olfaction (i.e. smelling). The compositions and methods are useful in treating diabetes type 2 in individuals.

Most generally, the present invention provides for a method of inducing the production of insulin in the body by an individual smelling a composition of a solution including testosterone, and inducing the production of insulin in the body of the individual.

Preferably, the composition is a solution of testosterone that provides an olfactory stimulus through its vapor. Preferably, testosterone is dissolved in an alcohol to create a solution. The alcohol can be grape, ethanol (i.e. ethyl alcohol), or other grain alcohols. A dose of the composition for administration can include 50 to 10,000 nanograms of testosterone. For example, one spritz or application of the solution can contain 200-500 nanograms of testosterone. Only a few hundred molecules of testosterone are necessary to induce a response in the body. When molecules are inhaled in the nose, they attach to specific receptors in the olfactory bulb. The molecules attach to receptors causes their unique vibratory signature to send their specific stimulus to the hypothalamus. This signals the brain to initiate production of insulin.

The composition can be in the form of a pharmaceutical composition or a nutraceutical composition. The pharmaceutical or nutraceutical composition is preferably a topical composition for application to the skin although there is no requirement that it be applied to the skin before sniffing. It can be sniffed directly from a container. The composition can be applied to any part of the skin, such as, but not limited to, the wrist or the upper lip, much like a perfume. The testosterone can be added to a pharmaceutically/nutraceutically acceptable carrier of alcohol or oil that still allows for the olfaction of testosterone. Preferably, the carrier is alcohol because it evaporates easily from the skin; however, any other appropriate carrier (such as oil or cream) can be used. Furthermore, while not preferred in combination with the alcohol carrier, any other pharmaceutical or nutraceutical excipients can also be used where appropriate. The amount of testosterone in a pharmaceutically or nutraceutically effective amount can be determined by one skilled in the art but generally is in an amount to increase the levels of insulin and reduce blood sugar in an individual and return the insulin levels to a normal level.

The composition of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

The doses can be single doses or multiple doses over a period of several days, or daily or weekly treatment. The treatment generally has a length proportional to the length of the disease process and drug effectiveness and the patient species being treated.

The present invention also provides for a method of treating diabetes type 2 by an individual having diabetes type 2 smelling a composition of a solution including testosterone, inducing the production of insulin in the body of the individual, and treating diabetes type 2 in the individual. The individual can smell the composition at any appropriate time interval to induce production of insulin, such as daily, weekly, or monthly. By smelling the composition, the need for insulin injections is eliminated. However, the method can also be performed in combination with insulin therapy.

In the present invention, as described in Example 1, a study was designed to measure sugar level in men before and after smelling testosterone. While the level of insulin in the blood following insulin olfaction was not directly measured, the observed blood sugar level reduction is reliable evidence that insulin is produced. In current medical practice, a lowered blood sugar value is considered proof of insulin presence and utilization.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

Example 1

To evaluate the possible role of testosterone in blood sugar reduction in diabetes type 2, the following protocol was designed.

Ten men between the ages of 30 to 90 volunteered to participate in this study as subjects. Approximately one and a half hours after having a meal the subject came to Applicant's office. Prior to the testosterone olfaction the blood sugar level was measured.

The subject produced an adequately sized drop of blood from a finger using a lancing device. The blood sugar was measured with a Contour Blood Glucose Monitoring System, Model 9546 C, Serial Number FB00450. The drop of blood was picked up by a Contour blood glucose test strip 7097C specific for the instrument and within the usable date range. This value was recorded as mg/dL.

A drop of pure testosterone diluted 1:1000 in ethanol was sprayed onto the palm of the hand and smelled by the subject. Prior studies showed that other concentrations have essentially the same effect. This concentration more efficient than the undiluted hormone.

A second blood drop was immediately taken and measured and recorded in the same manner as described above.

TABLE 1 shows the recorded values.

TABLE 1

EXPERIMENTAL DATA mg/dL

| SUBJECT | AGE | BEFORE OLFACTION | AFTER OLFACTION | PERCENT CHANGE |
| --- | --- | --- | --- | --- |
| MS | 90 | 142 | 86 | 70 |
| JH | 83 | 183 | 98 | 53 |
| MM | 60 | 105 | 92 | 12 |
| XB | 68 | 142 | 99 | 30 |
| MW | 60 | 155 | 86 | 56 |
| WH | 65 | 142 | 99 | 30 |
| RL | 61 | 175 | 109 | 38 |
| BM | 82 | 132 | 107 | 19 |
| SE | 30 | 156 | 130 | 17 |
| RG | 75 | 238 | 158 | 34 |

All ten subjects showed some reduction in their sugar level after testosterone olfaction. The percent reduction varied from 12 to 70 with the average for all ten being 36 percent.

These tests show that testosterone olfaction lowers blood sugar in the time it takes to lance the finger and collect the blood and test, i.e. in about 30 seconds. The exact time for the blood level to drop may be faster than the test method could determine.

SUMMARY

The data shows conclusively that testosterone olfaction used alone lowers the blood sugar level. Further investigation may reveal a system for the control of blood sugar that functions concurrently with insulin or that may be a separate system specific to testosterone.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method of inducing production of insulin in an individual's body in an individual in need thereof, including the steps of:

an individual applying an effective amount of a composition including testosterone to their skin;

the individual smelling the composition on their skin; and inducing the production of insulin in the body of the individual.

2. The method of claim 1, wherein the composition is a solution of alcohol selected from the group consisting of grape, ethanol, and grain alcohols.

3. The method of claim 1, wherein the composition includes 50 to 10,000 nanograms of testosterone per dose.

4. The method of claim 1, wherein the composition is a topical composition for application to skin of the individual.

5. The method of claim 1, wherein said smelling step is further defined as smelling the composition from a part of the skin selected from the group consisting of a wrist or an upper lip.

6. The method of claim 1, wherein said smelling step is performed at a time selected from the group consisting of daily, weekly, or monthly.

7. The method of claim 1, wherein said inducing step further includes the step of reducing blood sugar levels in the individual.

* * * * *